(12) United States Patent
Macaulay et al.

(10) Patent No.: US 6,610,992 B1
(45) Date of Patent: Aug. 26, 2003

(54) ROTATING BEAM METHOD AND SYSTEM FOR MEASURING PART EDGES AND OPENINGS

(75) Inventors: Donald Macaulay, Apopka, FL (US); Robert Macaulay, Roswell, GA (US); George Macaulay, Apopka, FL (US)

(73) Assignee: Clasmet, Apopka, FL (US)

( * ) Notice: Subject to any disclaimer, the term of this patent is extended or adjusted under 35 U.S.C. 154(b) by 0 days.

(21) Appl. No.: 09/908,783

(22) Filed: Jul. 18, 2001

Related U.S. Application Data
(60) Provisional application No. 60/219,720, filed on Jul. 19, 2000.

(51) Int. Cl.[7] .............................................. G01N 21/86
(52) U.S. Cl. ........................... 250/559.22; 250/559.36; 356/614; 356/239.1
(58) Field of Search .......................... 250/234, 559.36, 250/559.22, 559.24, 559.25, 559.4, 559.44, 235, 236; 356/237.1, 394, 398, 614, 239.1

(56) References Cited

U.S. PATENT DOCUMENTS

| | | | | |
|---|---|---|---|---|
| 3,806,252 A | * | 4/1974 | Harris et al. | 356/156 |
| 3,886,372 A | * | 5/1975 | Sanglert | 250/571 |
| 4,647,208 A | * | 3/1987 | Bieman | 356/375 |
| 4,711,579 A | | 12/1987 | Wilkinson | 356/615 |
| 5,159,202 A | * | 10/1992 | Ametani | 250/561 |
| 5,184,217 A | | 2/1993 | Doering | 348/88 |
| 5,291,270 A | | 3/1994 | Koch et al. | 356/602 |
| 5,319,442 A | | 6/1994 | Rosser | 356/615 |
| 5,351,078 A | | 9/1994 | Lemelson | 348/135 |
| 5,403,140 A | | 4/1995 | Carmichael et al. | 414/208 |
| 5,504,345 A | | 4/1996 | Bartunek et al. | 250/559.4 |
| 5,636,031 A | | 6/1997 | Passoni | 356/394 |
| 6,011,255 A | | 1/2000 | Rueb et al. | 250/234 |
| 6,044,288 A | * | 3/2000 | Wake et al. | 600/407 |
| 6,066,845 A | | 5/2000 | Rueb et al. | 250/234 |
| 6,441,908 B1 | * | 8/2002 | Johnston et al. | 356/602 |

* cited by examiner

*Primary Examiner*—Stephone B. Allen
*Assistant Examiner*—Christopher W. Glass
(74) *Attorney, Agent, or Firm*—Brian S. Steinberger; Law Offices of Brian S. Steinberger P.A.

(57) ABSTRACT

A dual beam concentric polar axis scanning machine for allowing flat parts to be easily scanned and measured. Flat shaped parts are placed on a glass datum type part support surface. The dual beam laser type scanners are positioned on a motion stage beneath the part support surface and move in the x and y planes parallel to the part support surface. Detectors above the surface receive the beams and move in unison with the scanners. Initially, the beams trace the external outline of the part and measure all grooves, side indentations and the like. Next, the beams pass over the surface of the part locating and mapping the locations of any openings therethrough. Finally, the beams trace perimeter edges of each of the openings for their measurements. The dual beams include an outer rotating beam also referred to as a forward looking beam, and an inner rotating beam where the forward looking beam restricts the inner a beam to continuously and consistently measure the exterior side edges of the part, the opening locations in the part, and the side edges of the openings of the part.

16 Claims, 6 Drawing Sheets

360° = 4000 Divisions

ROTATING BEAM METHOD AND SYSTEM FOR MEASURING PART EDGES AND OPENINGS

This invention relates to optical scanners, and in particular to methods and apparatus for using laser beams to accurately and quickly measure side edges and through-hole openings in complex shaped flat parts in two dimensions through optical scanning, and this invention claims the benefit of U.S. Provisional application No. 60/219,720 filed Jul. 19, 2000.

BACKGROUND AND PRIOR ART

Flat type parts of different sizes generally need to be duplicated or reverse engineered for a multitude of reasons. For example, gaskets on antique type automobiles may not be easily available and thus would need to be reduplicated. A gasket on an internal combustion engine can generally include a flat metal type part shape having unique side edges and unique through-holes for fasteners, manifold openings, and the like.

In addition to duplication purposes, the inspecting of flat shaped parts such as metal parts, in order to verify tolerance compliance to specific dimensional limits, requires high degrees of accuracy.

Precise part measurements of the parts can then be then be placed into known laser burning machines to produce the parts. Several types of techniques have been known over the years to measure parts but are known to be problematic.

Part measurements and inspections have included the use of CCD (charge coupled devices) arrays and cameras. See for example, U.S. Pat. No. 4,711,579 to Wilkson; U.S. Pat. No. 5,184,217 to Doering; U.S. Pat. No. 5,319,442 to Rosser; U.S. Pat. No. 5,351,078 to Lemelson and U.S. Pat. No. 5,636,031 to Passoni. However, the use of these elaborate sensor arrays and cameras require multitudes of components and equipment, and extensive construction and operation that can all be expensive, time consuming, and not be able to provide accurate precise measurements of the parts.

Other types of approaches have included the use of laser systems. See for example, U.S. Pat. No. 6,011,255 to Rueb; and U.S. Pat. No. 6,066,845 to Rueb et al. (the Virtek Vision Corporation patents). In these types of systems, a laser beam probe scanning system moves a single small diameter collimated beam from a fixed position scanner located five feet above and centered on a 4 by 4 foot square glass datum. The beam scans the part at high speed, steered by two galvanometer mirrors, tracking the part's edge by keeping the beam half on and half off it's edge. The half off the edge portion of the beam is reflected back to the scanner by a flat high resolution, vinyl retro reflector, mounted below the datum glass, off each galvo mirror, off a beam splitter mirror to a photo diode detector. In these types of systems angular distortion is a major problem in this design (the only true reading would be when the beam is perpendicular to the datum). For instance, all round holes scanned with the beam at an angle are seen as ovals, it's narrow dimension is shortened additionally because the beam can only measure the top near side and far side bottom of the hole, which precludes measuring the hole's width. All this distortion gets greater as the angle of the beam to the datum gets greater when scanning features at greater angles on larger and larger parts. It also gets greater as the part gets thicker. This distortion is corrected in software, based on the thickness of the part and the angle of the scan beam to the datum at the instant any feature is measured. There can be other types of problems with these systems as listed below with other laser systems.

Additional types of laser type systems have also been disclosed. See for example, U.S. Pat. No. 5,291,270 to Koch; U.S. Pat. No. 5,403,140 to Carmichael et al.; and U.S. Pat. No. 5,504,345 to Bartunek et al. However, the laser systems known to the inventors also have problems. For example, these systems generally require the part be placed in an exact location for measurement purposes, where having the part off position can provide erroneous measurements. In addition, these systems generally rely on reflection and/or backscattering of the signal where many distance measurements must be calculated which can also result in erroneous measurements. Furthermore, another general problem with these systems is that the radiating signals can over-run the sides of the object being scanned, and can require the measurements having to be restarted from scratch resulting in extra time and cost for the measurements.

In addition to the above patents, businesses have also tried to inspect parts. One of the subject inventors, Don Macaulay, was the principal engineer in developing high speed optoelectronic parts flaw inspection and dimensional inspection machinery for RCA Industrial Automation Systems, Plymouth, Mich. between February 1966 and August 1969, and for Sensors Inc. of Ann Arbor, Mich. between October 1970 and May 1972. The machinery included linear arrays of photo diodes and HeNe laser sources that were no better than the prior art of record described above, in that these devices were incapable of accurately and easily and economically detecting exterior side edges opening locations and side edges of the openings in parts that needed to be duplicated and/or inspected. Thus, the need exists for solutions to the above stated problems.

SUMMARY OF THE INVENTION

The first objective of the present invention is to provide a system for inspecting and measuring parts by placing a part in a stationary non specific position adjacent a scanning signal.

The second objective of the present invention is to provide a system for inspecting and measuring parts that allows the parts to be quickly and easily scanned and measured.

The third objective of the present invention is to provide a system for inspecting and measuring parts that allows for easy reverse engineering of the part.

The fourth objective of the present invention is to provide a system for allowing parts to be continuously inspected and measured without having to restart the measurements of the parts.

The fifth objective of the present invention is to provide a system for inspecting and measuring parts with a look ahead signal for allowing only the part to be measured.

The sixth objective of the present invention is to provide a system for inspecting and measuring parts by eliminating any angular distortion that would need to be corrected. The invention always scans the part with the beam or beams perpendicular to the datum.

The seventh objective of the present invention is to provide a system for inspecting and measuring parts having a resolution at least 50 times greater than an angular scan system.

The eighth objective of the present invention is to provide a system for inspecting and measuring parts having an improved signal to noise ratio. The invention does not use a beam splitter mirror as used in an angle scan system does which can lose 75% of it's beam strength.

The ninth objective of the present invention is to provide a system for inspecting and measuring parts that does not require a retro-reflector (exact losses unknown) but quite high due to scattered return beam light reflected at angles which cannot return to the scanner optics.

The tenth objective of the present invention is to provide a system for inspecting and measuring parts using a scan circle that provides a constant beam circular scan velocity.

The eleventh objective of the present invention is to provide a system for inspecting and measuring parts that uses a small diameter collimated scan beam which provides higher resolution measurements (the resolution of measurement being inverse to scan beam to diameter).

The twelfth objective of the present invention is to provide a system for inspecting and measuring parts that uses a cylindrical shaped scan circle that provides precise geometric type measurements of edge and through-hole diameters.

The thirteenth objective of the present invention is to provide a system for inspecting and measuring parts using a scan beam's rotation at high speed in a small diameter circle to make 133 measurements per second of the part's edge or features at approximately 0.00004 to approximately 0.00015 inch resolution. While for XY motion system's servo tracking purposes, the scan circle is treated as a spot 10 to 40 times the diameter of it's scan beam diameter. This allows for much greater XY axis scanner tracking speeds than would be possible if the system had to keep only it's very small scan beam tracking the part's edge.

A system and method for optically measuring and inspecting parts is described. The system and method can include a support surface having a transparent portion for supporting a part thereon. An optical beam generator such as a laser generates a collimated laser beam along a perimeter side edge of the part. A detector such as a photo diode, on the opposite side of the support surface detects the portion of the laser beam not stopped by the part's edge. An XY motion stage that can be located below the support surface can be moved by a servo type motor which moves the optical beam generator and the detector above the support surface in unison about the perimeter edges of the part. A computer can receive the detected optical beam and provide x and y coordinates of the perimeter edges of the part. Next, the XY motion stage can be used to scan a surface portion of the part with the optical beam and the detector moving in unison, and locate x and y coordinates for openings in the part. Finally, the XY motion stage can move the optical beam and the detector in unison about perimeter edges of the openings in the part, and provide x and y coordinates of the perimeter edges of the openings in the part.

The optical beam can include two beams one beam for tracing the edges of the part, finding the openings in the part, and tracing the edges of the openings, and a second beam for continuously and consistently keeping portions of the first beam on the part. Separate photo diodes can be used for each of the beams The two beams can include an outer rotating look ahead beam, and an inner rotating scan beam concentric to the outer beam. Both beams rotate at the same rpm and move at a constant speed across the part's edges and surface. Both beams can decelerate down to a full stop with their common center on one of: a corner of the perimeter edges of the part, an edge of the surface of the part, and a corner of interior edges of the openings of the part. A working example has both beams rotating at approximately 4000 rpm, and moving at approximately 5 inches per second. A working example of the inner beam has a beam diameter of approximately 0.005 to approximately 0.02 inches, rotating in a circle approximately 05 to approximately 0.2 inches (adjustable ) in diameter. The working example further has the outer beam approximately 0.20 inches in diameter, rotating in a circle approximately 3 inches in diameter. Beam rotational speed and scanner moving speeds can be changed using keyboard commands. Non adjustable beam diameters and scan circle diameters, can be changed using optional quick change scanner heads.

Further objects and advantages of this invention will be apparent from the following detailed description of a presently preferred embodiment which is illustrated schematically in the accompanying drawings.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Figure 1:
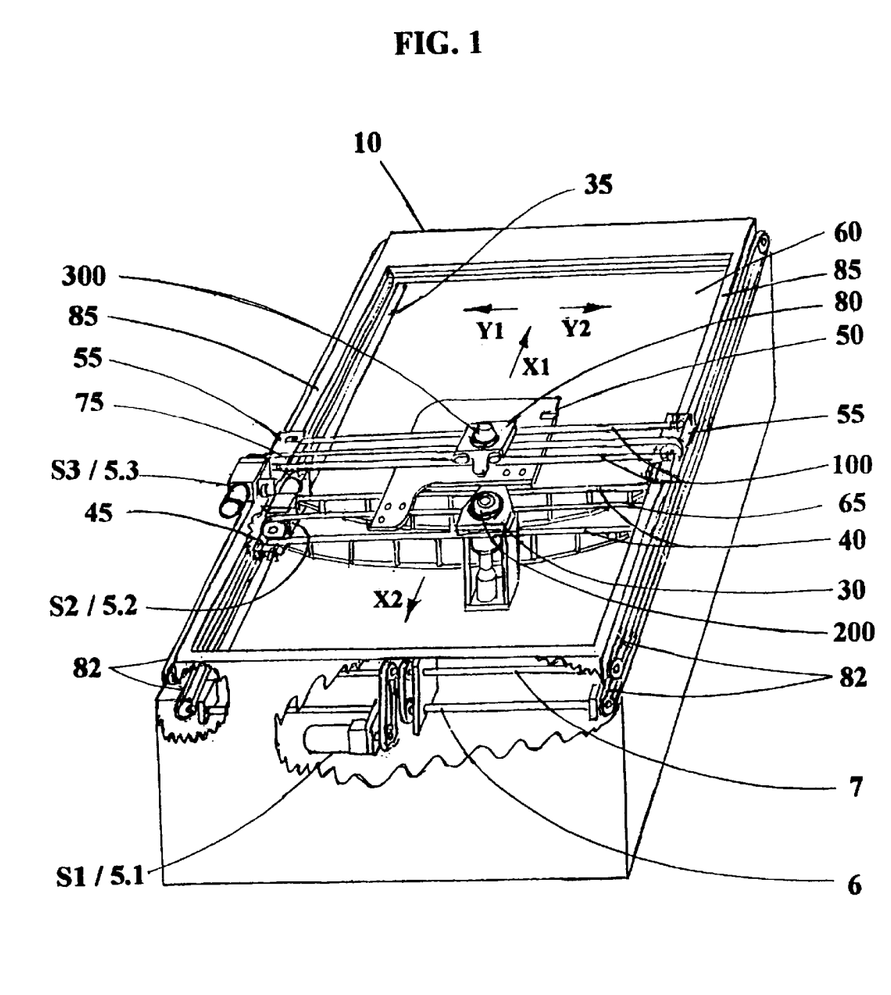
FIG. 1 is a perspective view of a preferred embodiment of the coordinate measuring system laser beam type of the subject invention.

FIG. 1 is a perspective view of a preferred embodiment of the coordinate measuring system laser beam type system 1 of the subject invention, which can be used to measure complex shaped parts, such as flat parts, in two dimensions, up to approximately 1 inch thick. The system 1 consists of a base cabinet unit 10 and a computer to be described in detail later. The top 60 of the base unit 10 top can be an optically transparent type material such as but not limited an approximately 15 mm thick transparent plate glass datum (hereafter "the datum") on which the part 50 to be measured is placed. Unlike, other prior art systems, the part 50 does not have to be placed in an exact location on the datum. The invention can operate by having the part 50 placed off-center and or rotated on the datum 60. The part 50 can be a flat type part such a sheet of flat metal such as for example a gasket. Specific information such as describing the part's 50 size, shape, details or it's orientation as placed on the datum 60 is not required. The parts 50 outside edges and the edges of all it's through features such as holes, slots, and the like, are scanned and measured by collimated laser beams projected from below by an optical beam scanner 200. The scanner 200 can be located underneath the datum 60 and can include an XY motion stage dolly 30 which can ride in the directions of arrows Y1, Y2 on gantry track assembly 40 which mounts on two X axis track dollies moving in the direction of arrows X1,X2, on tracks 35 located on both sides within the cabinet 10. On the top of the cabinet 10 can be a detector 300 for detecting optical signals from the scanner 200. The detector 300 can include its' own XY motion stage dolly 80 which can ride in the directions of arrows X1, X2 on X axis tracks 85 on both sides of the cabinet 10. The detector 300 can also include a Y axis gantry track 100 which allows the detector 300 to be able to move in the direction of arrows Y1 and Y2. A servo motor 5.1 can be used to move the scanner 200 and detector 300 in unison in the direction of the X1,X2 arrows above and below the datum 60 with the part 50 between the scanner 200 and detector 300. A servo motor 5.2 can be used to move the XY motion scanner dolly in the direction of the Y1,Y2 arrows. A servo motor 5.3 can be used to move the detector dolly 80 in the direction of the Y1,Y2 arrows.

Figure 2:
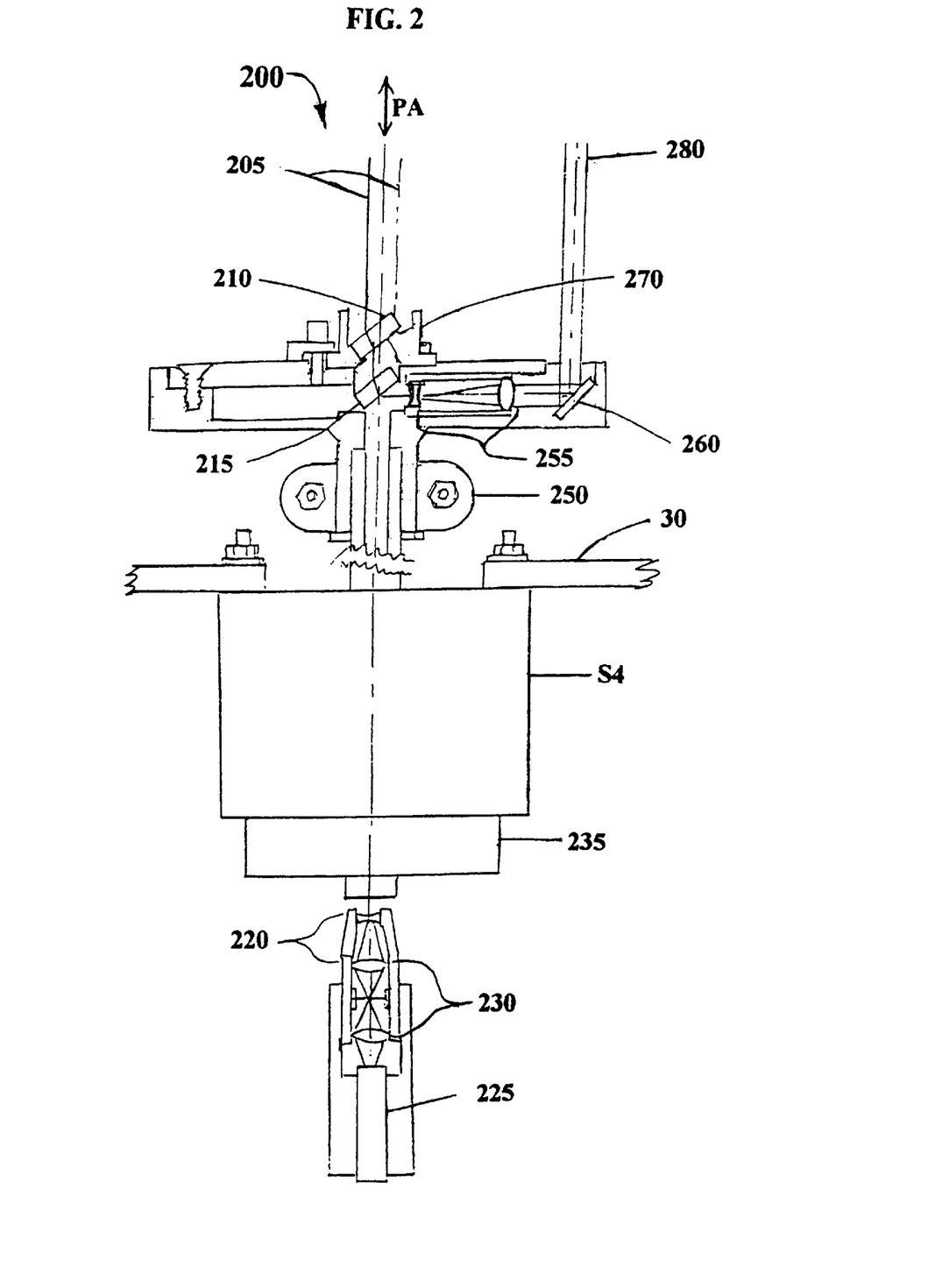
FIG. 2 is an enlarged side view of the dual concentric beam polar axis scanner of FIG. 1.

FIG. 2 is an enlarged side view of the dual concentric beam polar axis scanner 200 of FIG. 1. Scanner 200 include an adjustable refractive window 210, custom sized to spec. fused silica anti reflective coated (AR) both sides. Beam splitter window 215, same as 210 except one side only AR coated, other side can be approximately 50% reflective coating, and beam diameter reducer/collimator 220. LED (light emitting diode) point source 225, such as an approximately 806 nm point LED (infrared laser source) or visible red units. Spatial filter 230, can be used, and 1K pulse per revolution optical encoder/generator, stock unit several sources. Other components that can be used include a P.M. Brushless hollow shaft motor, Eastern Air Devices, and a scanner mounting clamp 250, made by CGI Inc, and a beam expander 255 that uses two small lenses one+and one−focal length, and a front surface mirror 260. Small beam 205 can be an approximate 0.005 diameter collimated high resolution beam that rotates in a scan circle having a diameter that can be adjusted to be between approximately 0.05 inches to approximately 0.128 inches. Component 270 can be a hat shaped brass detail in which window 210 is mounted (cemented) at a 45° angle. It's rim can be set in a shallow recessed round nest in the brass scanner head, and held in place by three dogs, and their locking screws, and can be set to any angular position to the fixed window 215 below. In the position shown, component 270 doubles the beam offset provided by the 215 window below. If loosened and rotated approximately 180° from the position shown, it cancels all of the beam offset provided from below. Adjusting it to angles between these two extremes provides any beam offset from maximum to zero.

The look ahead beam 280 can be a collimated beam having a diameter of approximately 0.15 inches to approximately 0.25 inches and can rotate in a large scan circle having a diameter of approximately 3 inches. Both beams 205 and 280 can rotate in exact angular synchronization in the same direction around the scanner's polar axis, PA. The look ahead beam 280 continuously looks ahead and tells the systems components such as the servo motors (to be later described in detail) to stop, move, and the like. The small scan circle beam 205 does the actual measurements of the parts side edges, through-hole opening locations, and side edges of the through-hole opening locations.

The 225 point source LED projects a divergent beam into spatial filter 230 which cleans up the beam. The beam is then shrunk and collimated in component 220 and projected up through the hollow scanner motor shaft, into the scanner head. Half of the beam is split off approximately 90 degrees on striking window 215. Then the beam passes through beam expander 225. Expanded to it's larger diameter it is rotated again approximately 90 degrees by front surface mirror 260 and is projected up approximately 1.5 inches from, and parallel to the axis of rotation of the scanner motor. As the scanner head 200 rotates at approximately 4,000 rpm. this beam traces in an approximately 3 inch diameter scan circle. The other 50% of the original beam passes through the beam splitter window 215 where it is refracted at an angle and exits the window displaced off axis but restored parallel to the axis of scanner rotation. It then proceeds up, through refractive window 210 where it's off axis displacement is can be adjusted manually by changing by the radial positing of window 210, as described above.

Figure 3:
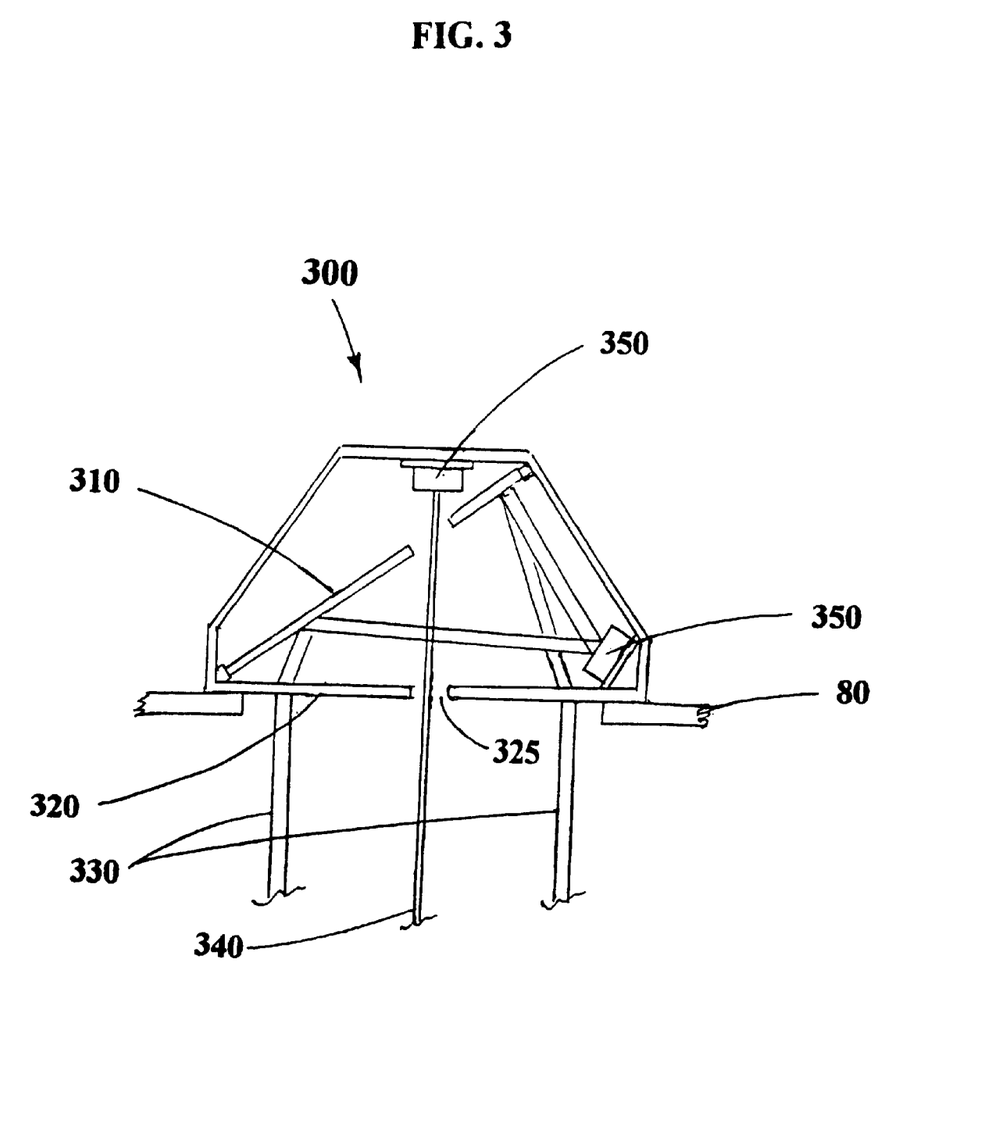
FIG. 3 is an enlarged side view of the dual beam detector assembly of FIG. 1.

FIG. 3 is an enlarged side view of the dual beam detector assembly 300 of FIG. 1. The components and labels of FIG. 3 can include a front surface mirror 310, fresnel lens 320, photo diode detectors 350, such as an Edmund Scientific H54034, large scan circle 330, small scan circle 340, and XY axis motion stage dolly 80. Detector 300 moves on its' own servo motor driven XY motion stage 80, tracking the polar axis, PA, of the scan projector 200 scanning the part from below (as shown in FIG. 1). The small beam scan circle always projects up, through the central hole 325 in fresnel lens 320 and on to it's photodiode detector 30. The look ahead beam circle 330 rotating at 4,000 rpm scanning it's 3 inch diameter scan circle continually passes through the fresnel lens, its' center of rotation on the optical center of the lens. The fresnel lens focuses the approximately 3 inch diameter beam to a point at it's focal point approximately 4.5 inches above, the front surface mirror 310 redirects the focal point and the beam to continually fall on it's stationary photodiode detector 350, which, continually reading the light value of beam, detects every transit of the beam on the part 50, off the 50 signal as it transits the part's edge.

Figure 4:
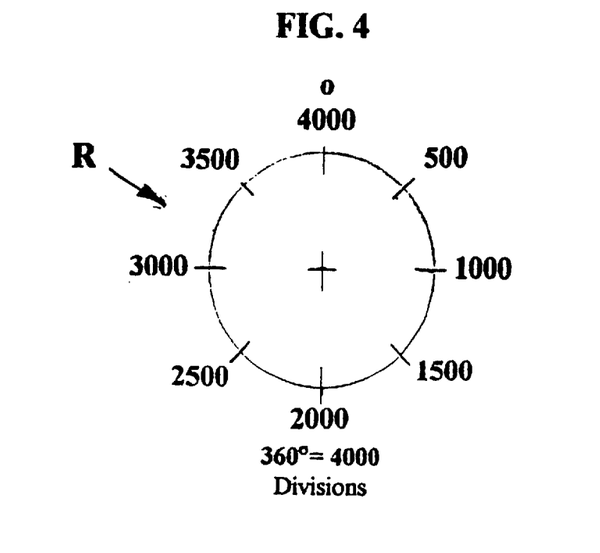
FIG. 4 shows a view of a scan circle with division markings along the circle.

FIG. 4 shows a view of a scan circle R, with division markings along the circle. The circle R, can be representative of both the rotating small beam 205 (FIG. 2)/340 and the rotating large beam 280/330. The 360 degrees of the circle R can be divided into 4000 increments for measuring purposes. A DC motor described later in reference to FIG. 6 drives the scanner 200, rotating both beams at approximately 4000 rpm (revolutions per minute), and also provides an integral optical pulse encoder/generator (described in detail in reference to FIG. 6) providing a single pulse, and a second output of exactly 1,000 pulses per revolution. Read in quadrature (multiplied by four), the output has the result of dividing each complete rotating scan circle into 4,000 individual radial angular measurement increments.

As previously described small beam 205 (FIG. 2)/340 can be an approximate 0.005 diameter high resolution beam that rotates in a scan circle having a diameter that can be adjusted to be between approximately 0.05 inches to approximately 0.128 inches. The look ahead beam 280/330 can be a collimated beam having a diameter of approximately 0.15 inches to approximately 0.25 inches and can rotate in a large scan circle having a diameter of approximately 3 inches. Both beams 205 and 280 rotate in exact angular synchronization around the scanner's polar axis, PA.

Figure 5:
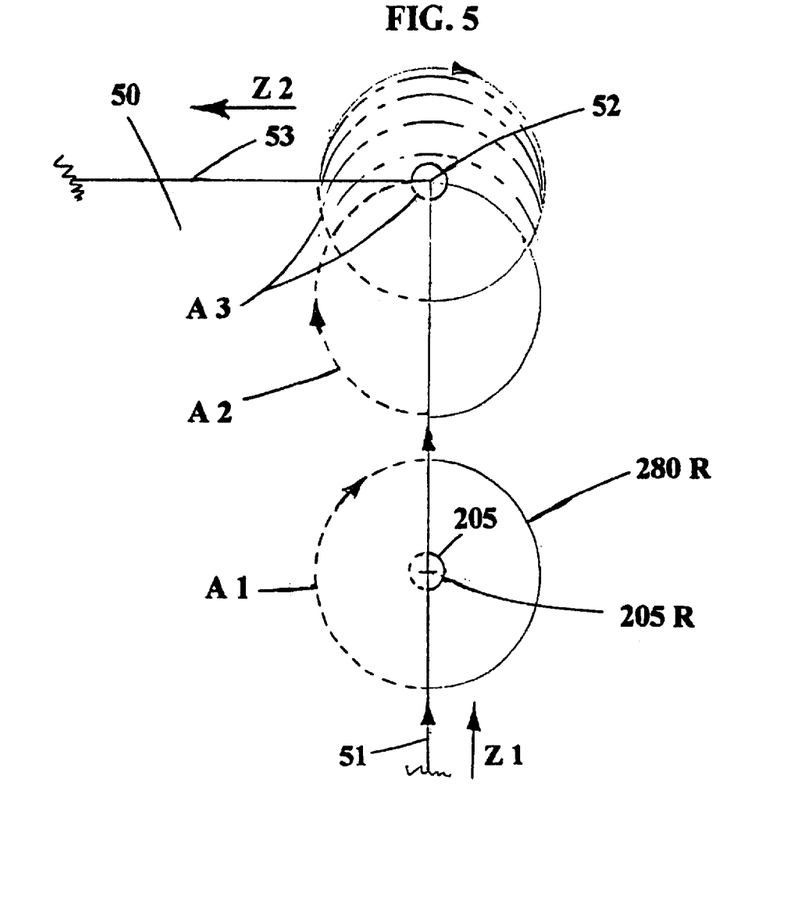
FIG. 5 shows a view of the dual concentric beams moving along and edge and corner of a part.

FIG. 5 shows a view of the dual concentric beams 205R and 280R moving in the direction of arrow Z1 along and edge 51 of the part 50 each rotating at approximately 4000 rpm with the circles moving at approximately 5 inches per second. Initially, beam 205 rides along the outer edge 51 of the part so that arc A1 encompassing half the circles of the beam circles 205R, 280R have increment divisions from 0 to 2000 divisions off the part 50, and increments 2001 to 4000 on part 50 look ahead circle 280R, the speed of approximately 5 inches per second remains consistent as shown by arc A2 of another position of the circles 205R, 280R. The look ahead circle 280R detects the corner 52 of the part 50 and the speed of the circles movement decelerates to zero velocity on the corner 52 of the part 50. The small arc A3 reading between approximately 2000 to approximately 3000 divisions provides a radial edge detection signal allowing for a new compass heading of the edge 52. Next, the beam circles 205R, 280R start moving in the direction of arrow Z2 along another edge 53 of the part 50 at the constant speed of approximately 5 inches per second until another corner, edge of the like occurs. Although, the circles 205R, 280R are shown with half the circle on the part, the invention can work with less than half the circles on the part. The invention can use the system block diagram shown and described in reference to FIG. 6.

Figure 6:
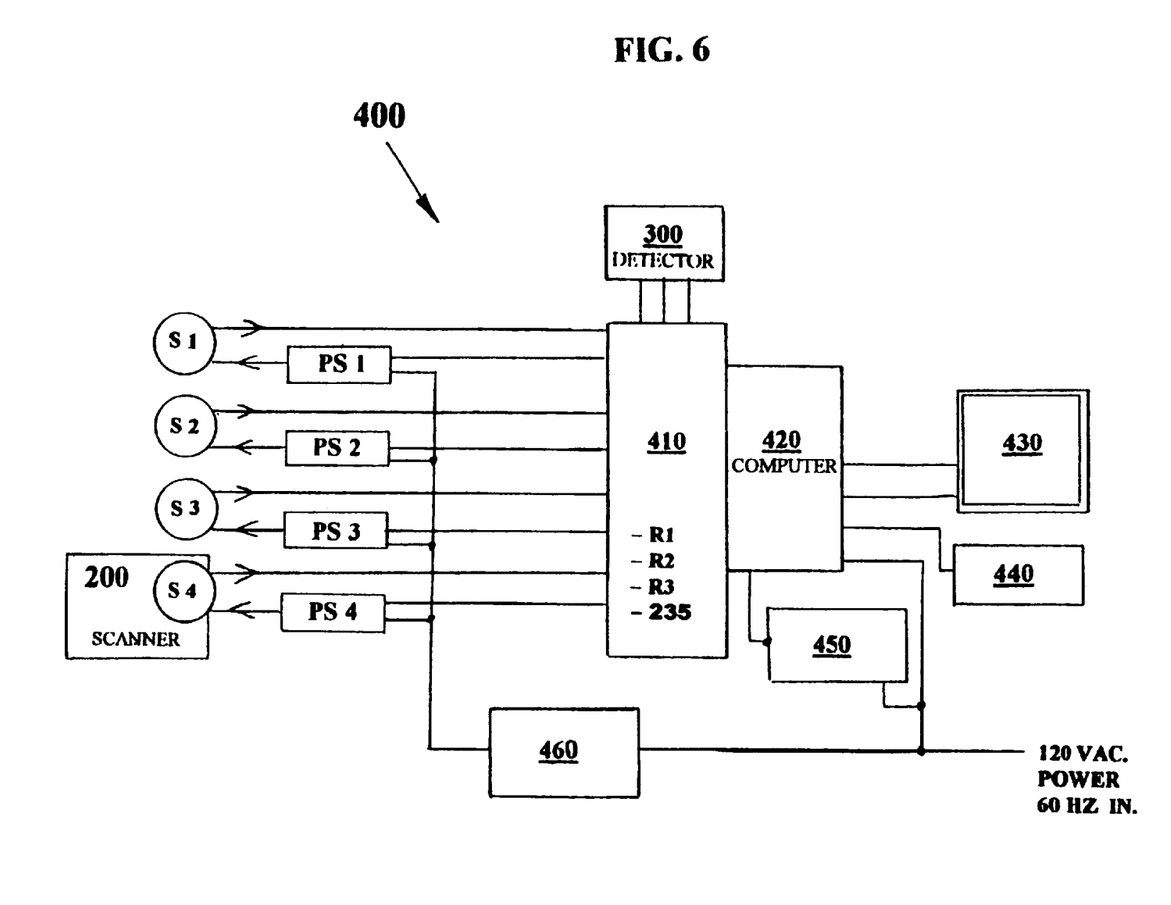
FIG. 6 is a schematic block diagram of the components used to control the measuring system laser beam type of the above figures.

FIG. 6 is a schematic block diagram 400 of the components used to control the measuring system laser beam type of the above figures. Referring to FIG. 6, S1, S2, S3 and S4 are the motors that can be used with the invention 1 of FIG. 1. S1 and S2 refer to the DC gear reduction motor with pulse generator for the X & Y axis drive, S3 refers to the DC gear reduction motor with pulse generator for the detector Y axis drive, and S4 refers to the DC drive motor with hollow shaft and integral pulse generator.

Referring to FIG. 6, PS 1, 2, 3 & 4 refer to the PWM brushless motor DC power supplies. Controller 410 can be a Delta Tau UMAC programmable multi-axis controller which controls all four motors. Computer 420 can be a Delta Tau PC-104 digital computer. And is equivalent to a Pentium 686, 233 MH. The remaining Monitor 430, Keyboard 440, and printer 450 can be conventional components available basic computer applications.

Referring to FIG. 6, DC power supply 460 supplies power to the four DC brushless motor power supplies PS 1, 2, 3, & 4. Because the brushless motors have no communtators, external switching power supplies are required. These provide pulse width modulated power (PWM) for accurate speed control. The monitor 430 can provides interactive control to the machine operator for certain choices available and it also can display the part 50 (FIG. 1) as a drawing progressing as it's features are being measured. As in any computerized system, the keyboard 440 is the means which the operator communicates with the system 400. Such inputs as selecting the output record he selects on a given inspection task. The printer 450 will provide drawings of the inspected part 50 with a list of any dimensions and features marked that are out of tolerance. The system 400 describing the part 50 and the computer 420 also contains floppy disk drive to in put drawing data into the computer and will output data for manufacturing data on reversed engineered parts.

Figure 7:
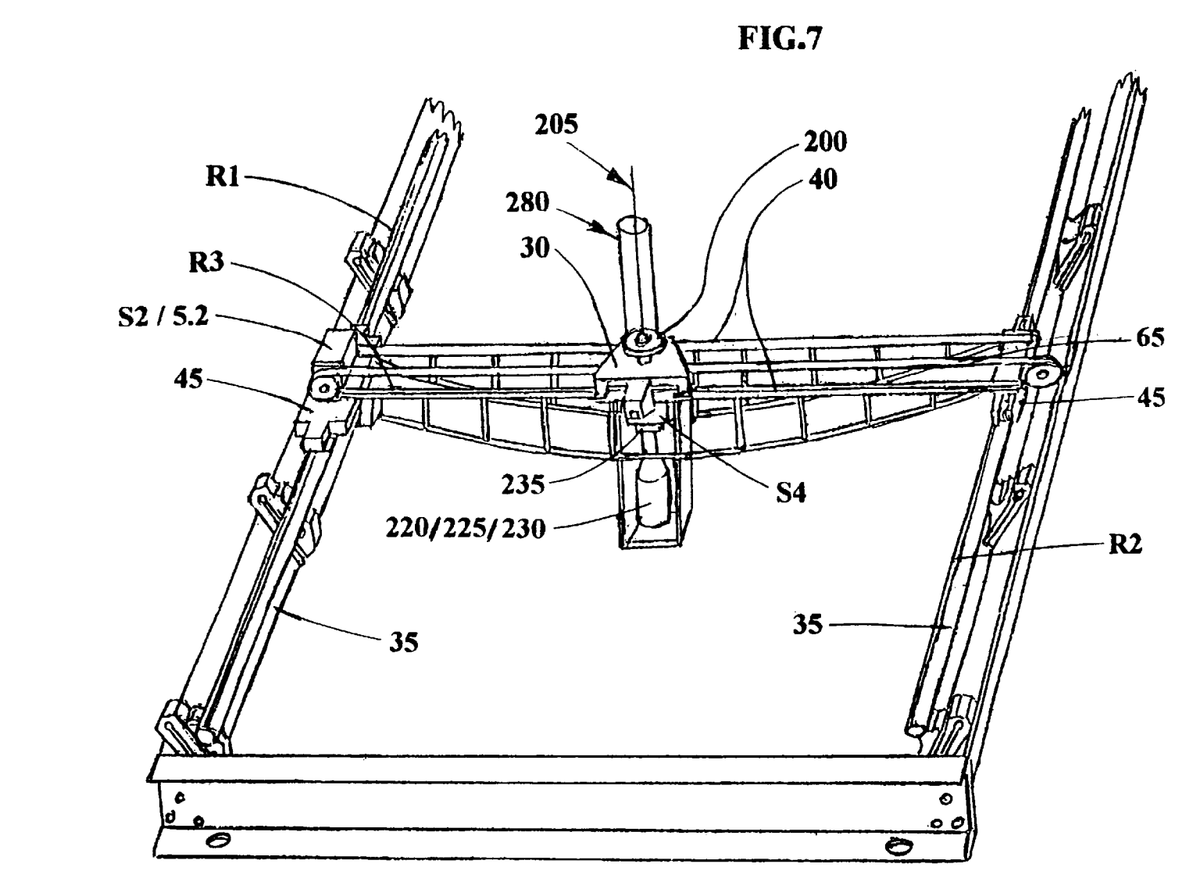
FIG. 7 is shows the dolly and track system that can support the scanners and detectors for the preceding figures.

FIG. 7 is shows the dolly and track system that can support the scanners and detectors for the preceding figures.

Referring to FIGS. 1, 6 and 7, DC gear reduction motor S1/5.1 drives two drive shafts 6 and 7 at their centers using conventional toothed belts and precision metal toothed sprockets. Each shaft 6, 7 drives two long belts 82, one on each side of the machine 1. One shaft and its two long endless belts drive the each of two scanner (200) X axis track dollies 30, and the other shaft likewise drives the detector's two X axis dollies 80. Each of these precision endless belts is kept taut by conventional spring loaded pulleys around which the belts run, at the far end of the machine from the drive shaft end.

Referring to FIGS. 1, 6 and 7, another similar motor, S2/5.2 is mounted on a X axis gantry support dolly and drives the Y axis dolly 30 on the Y axis as required using a smaller endless toothed belt. A third similar smaller motor S3/5.3 is mounted on one of the detector X axis dollies and drives the detector dolly 80, in the Y axis also using a toothed belt. All three of these toothed belt drives keep their belts taunt by conventional type spring loaded return pulleys.

Referring to FIG. 7, R1 and R2 refer to the main X & Y axis track encoders such as one manufactured by Renishaw Inc., and R3 is the Y axis scanner track encoder also such as one manufactured by Renishaw Inc. The R1, R2, and R3 optical encoders can be mounted in both X axis track dollies and in the Y axis dolly. Additionally, their optical tape digital scale tapes can be bonded to the two X axis tracks and one Y axis track. These optical linear encoders can be super high resolution non contact devices with a measurement resolution of approximately five microns. The pulse generators (optical encoders R1, R2, R3 and 235) can be shaft driven by the motors S1–S4, and can come as a part of the motor. The one 235 we are using on the scan motor S4 outputs can output a single pulse each revolution on one output line, and approximately 1,000 pulses per revolution on another out output line. Their 1,000 pulse output can be read by the Delta Tau computer card in quadrature which multiplies the pulses to 4,000 pulses per revolution. Each revolution, the computer 420 (See FIG. 6) counts the pulses starting at one, each time the single pulse occurs. When an edge is detected, the computer 420 sends the count total at that instant (and continues to count) to a routine where the count is multiplied by the distance increment for each count (a very small micro dimension) the sum value which is the distance around the scan circle in angular terms, where the edge was detected, is converted from polar to XY coordinates, added to the XY coordinate location of the scan circle center when the detector pulse was received, and places this XY position of the parts edge into the memory map of the part being measured. Each revolution of the scanner shaft, the counter is reset to zero by the single scan motor pulse generator's single pulse, and the process starts over.

Referring to FIGS. 1–7, the polar and XY coordinate summing features will now be described. The system software in computer 420 can move the scanner 200 continually below the datum 60, and the detector 300 above the part 50 in the X and Y axis, tracing the part's edges 51–53 and features adjoining the edge (such as corner 52) slots, or any through feature which adjoins the part's edge keeping the traced edge 51, 53 within the small scan circle 205. At each transition of the scan circle's beam on and off the part's edge, the detected edge signal strobes the probe beam's radial angle position, on it's scan circle, converts it's polar value to XY coordinates and adds it to the XY coordinate position of the scan circle's center point, strobed by the same detection pulse. This adjusted sum, the precise XY coordinate location of the part's edge at detection, is placed in the computers digital part map being plotted as the scan circle (205R) progresses on it's edge scan trace. This measurement can take place approximately 133 times per second. The diameter of the scan circle 205R can be adjusted, and the diameter of the individual beams 205, 280 can vary dependent on the application.

Referring to FIGS. 1–7, while the small beam scan circle 205R traces the part 50's outer edge 51, 53, the larger look ahead beam 280 rotating in exact angular synchronization with, and concentric to, the small beam scan circle 205R, precedes it on it's course by approximately 1.5 inches surveying the course changes ahead for the small beam scan circle 205R and provides the X Y axis motion system's computer program the course changes coming, which the small beam scan circle 205R must track. The system's computer 420 can process this data and provide the required deceleration, acceleration and velocity signals to the X Y motion system's servo drivers, to continually adjust the small beam scan circle's tracking speed, keeping it within it's own dynamic tracking authority envelope. This ensures it's tracking response will be adequate to follow the edge course changes, abrupt or otherwise, without running off the part's edge. The novel tracking velocity adjustment feature using the preview course data continually supplied by the larger diameter look ahead beam is one of the unique features of this dual beam polar axis scanner 200. This novel feature allows the system to track and scan part edges, at the highest velocity possible, for a servo motor driven XY motion system, of this type, compensating, in good measure, for it's nontrivial inertia.

The final part surface scan will now be described in reference to FIGS. 1–7. When the small beam scan circle 205R has completed measurement of the part 50s outside edges 51, 53 as described above, and the dimensions of size, shape, and location of these edges are in the system's memory part map within computer 420, the 3 inch look ahead scan circle 280R, operating in it's second, surface scan mode, scans the whole part 50s surface, in a fast, up and down overlapping pattern, locating and measuring, at low resolution, the shape, size and location of all through part features such as holes, slots, and the like, not joined with the parts outer edges, as previously described. This data is loaded into a preliminary map memory as the part 50s surface is scanned.

The final high resolution surface scan will now be described in reference to FIGS. 1–7. The high resolution small scan circle 205R now completes the scanning process. Moved by the X Y motion system to each feature located, measured, and logged into the preliminary map memory as described above, the system logic now moves the high resolution small beam scan circle over and around each of these through part features, tracing it's edges, measuring it's shape, size and location. These final precision scan dimensions are added to the memory part map as each feature is scanned, completing the part map. When the last feature is scanned, the scan projector 200 and it's detector 300 are parked in their home position at the end of the machine.

There can be a small door in one end of the base unit 10 cabinet at the home position provided for adjusting the small scan circle's diameter or changing it out.

The invention 400 is also able to provide a machine part inspection record output via the printer 450 or floppy disk in the computer 420. The Scanner 200 (FIG. 1) provides a digital signature fine resolution image of any part profile and all through surface features. This accurate image can be processed by the system software and compared to an existing Digital Template (any neutral format CAD (computer assisted drawing) file or supported proprietary CAD file image) verifying the accuracy/correctness of the scanned part. The output can also be in the form of a standard or custom dimensioned graphic print or any industry standard or proprietary CAD file format for viewing, manipulation or processing.

Although the preferred invention is primarily concerned with measuring through-hole openings, the invention can be used with detecting and measuring surface topography such as but not limited to indentations, craters, and the like, using the existing scanners and detectors, and/or including other optical sources and detectors that detect reflections off the part to measure distances for the surface configurations.

While the preferred embodiment describes positioning the scanner 200 below the datum, the invention can be practiced with the scanner on top of the datum or to one side of the datum.

Although the preferred embodiment has been described using LEDs, other types of laser type light sources such as Helium type lasers, and the like, can also be used.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method of measuring parts with an optical signal, comprising the steps of:
    (a) rotating an outer look ahead optical beam to determine portions of a part outside of perimeter edges and perimeter openings of the part;
    (b) rotating an inner scan optical beam concentric to the outer beam to measure the perimeter edges of the part and the perimeter edges of the openings, wherein the outer beam restricts the inner beam to measuring the perimeter edges of the part and the perimeter edges of the openings, and the outer and the inner beams are substantially perpendicular to the part;
    (c) tracing side perimeter edges of the part with the outer and the inner beams;
    (d) scanning over a surface of the part to locate the openings in the part with the inner and outer beams; and
    (e) tracing the perimeter edges of the openings with the inner and the outer beams, wherein the side perimeter edges, the locations of the openings and the perimeter edges of the openings provide a topographical measurement of the part.

2. The method of claim 1, wherein the part includes: a flat part.

3. The method of claim 1, wherein the outer rotating beam and the and inner rotating beam decelerates down from the selected distance per second value upon reaching at least one of: a corner of the perimeter edges of the part, an edge of the surface of the part, and a corner of interior edges of the openings of the part.

4. The method of claim 1, wherein the selected rpm value is approximately 4000 rpm, and the selected distance per inch value is approximately 5 inches per second.

5. The method of claim 1, wherein the inner beam has a beam diameter of approximately 0.05 inches to approximately 0.02 inches, and the outer beam has a beam diameter of approximately 0.2 inches.

6. The method of claim 5, wherein the outer beam rotates in a circle of approximately 0.05 inches in diameter, and the inner beam rotates in a circle of approximately 3 inches in diameter.

7. The method of claim 1, further including the step of:
    placing the part in a nonspecific position on a support surface, wherein the support surface has a transparent portion allowing the optical beam to transmit therethrough.

8. The method of claim 1, wherein the steps of tracing perimeter edges of the part, scanning the surface of the part and tracing edges of openings of the part includes the steps of:

moving an optical beam generator and an optical beam detector in unison about the support surface.

9. The method of claim 8, wherein the optical beam generator includes a laser, and the optical beam generator includes a photo diode.

10. A system for optically measuring and inspecting parts, comprising:

means for supporting a part on a surface having a transparent portion;

an optical beam generator for generating a rotating optical beam along a perimeter side edge of the part, the rotating optical beam being substantially perpendicular to the part;

a detector for receiving a portion of the rotating optical beam;

means for moving the optical beam generator and the detector in unison about the perimeter edges of the part; and means for providing x and y coordinates of the perimeter edges of the part;

means for scanning a surface portion of the part with the rotating optical beam and the detector moving in unison, wherein the provided means locates x and y coordinates for openings in the part; and means for moving the rotating optical beam and the detector in unison about perimeter edges of the openings in the part, wherein the provided means locates x and y coordinates of the perimeter edges of the opening in the part.

11. The system of claim 10, wherein the optical beam includes a laser, and the detector includes a photodiode.

12. The system of claim 10, wherein the rotating optical beam includes:

a first rotating beam for determining portions outside of the perimeter side edge of the part;

a second rotating beam to measure the perimeter side edge of the part, wherein the first rotating beam restricts the second rotating beam to measuring the perimeter side edge of the part, and the first and the second rotating beams are substantially perpendicular to the part.

13. The system of claim 12, wherein the first rotating beam and the second rotating beam include:

an outer rotating look ahead beam; and an inner rotating scan beam concentric to the outer beam, the outer and the inner beam having an identical axis, wherein the outer rotating beam and the inner rotating beam each rotating at a selected rpm value, and moving a selected distance per second value.

14. A method of measuring parts with a rotating optical signal, comprising the steps of (a) supporting a part in a non specific position on a surface;

(b) tracing along perimeter edges of the part with a rotating optical beam being substantially perpendicular to the part, and with a detector that together move in unison about the part; and (c) providing x and y coordinate measurements of the perimeter edges of the part;

(d) scanning over a surface of the part to locate openings in the part with the rotating optical beam and the detector moving in unison;

(e) tracing perimeter edges of the openings with the rotating optical beam and the detector moving in unison; and (f) providing x and y coordinate measurements of the locations and the perimeter edges of the openings in the part.

15. The method of claim 14, wherein the rotating optical beam includes the steps of:

providing a first rotating beam to determine portions outside the side perimeter edges of the part; and providing a second rotating beam to measure the side perimeter edges of the part, wherein the first beam restricts the second beam to measuring the side perimeter edges of the part, and the first and the second beams are substantially perpendicular to the part.

16. The method of claim 14, wherein the steps of providing the first rotating beam and providing the second rotating beam include the steps of:

rotating an outer look ahead beam; and rotating an inner beam concentric to the outer beam and continuously about the perimeter edges of the part.

* * * * *